(12) United States Patent
Staali et al.

(10) Patent No.: US 11,642,237 B2
(45) Date of Patent: May 9, 2023

(54) MULTICHAMBERED URINE COLLECTION DEVICE

(71) Applicants: Amine Staali, Mazouna (DZ); Souheil Guessoum, Algiers (DZ)

(72) Inventors: Amine Staali, Mazouna (DZ); Souheil Guessoum, Algiers (DZ)

(*) Notice: Subject to any disclaimer, the term of this patent is extended or adjusted under 35 U.S.C. 154(b) by 408 days.

(21) Appl. No.: 16/806,081

(22) Filed: Mar. 2, 2020

(65) Prior Publication Data
US 2020/0276046 A1 Sep. 3, 2020

Related U.S. Application Data

(60) Provisional application No. 62/812,985, filed on Mar. 2, 2019.

(51) Int. Cl.
*A61F 5/451* (2006.01)
*A61F 5/44* (2006.01)
*A61B 5/20* (2006.01)

(52) U.S. Cl.
CPC .............. *A61F 5/451* (2013.01); *A61B 5/202* (2013.01); *A61B 5/207* (2013.01); *A61F 5/4401* (2013.01); *A61F 5/4405* (2013.01); *A61F 5/4408* (2013.01); *A61F 2005/4402* (2013.01)

(58) Field of Classification Search
CPC ...... A61F 5/451; A61F 5/4401; A61F 5/4405; A61F 5/4408; A61F 2005/4402; A61B 5/202; A61B 5/207
USPC ........................................ 604/318, 347, 350
See application file for complete search history.

(56) References Cited

U.S. PATENT DOCUMENTS

| | | | | |
|---|---|---|---|---|
| 1,178,644 A | * | 4/1916 | Johnson | A61F 5/455 604/350 |
| 4,533,354 A | * | 8/1985 | Jensen | A61F 5/44 383/44 |
| 4,813,943 A | * | 3/1989 | Smith | A61F 5/4408 604/350 |
| 7,931,630 B2 | | 4/2011 | Nishtala et al. | |
| 8,308,705 B2 | * | 11/2012 | Lin | A61M 1/962 602/56 |
| 8,486,035 B1 | * | 7/2013 | Arce | A61F 5/449 2/72 |
| 2004/0059306 A1 | * | 3/2004 | Tsal | A61F 5/4404 604/332 |
| 2004/0176731 A1 | * | 9/2004 | Cheng | A61F 5/455 604/329 |
| 2013/0261573 A1 | * | 10/2013 | Rackley | A61F 5/4408 604/328 |

(Continued)

*Primary Examiner* — Andrew J Mensh

(57) ABSTRACT

A user friendly multi-chambered flat urine collection device comprising an inlet port having a non-return valve, an upper chamber further divided into a plurality of vertical chambers, a lower chamber further divided into a plurality of vertical chambers, a plurality of breathing open areas intervening said upper, lower and vertical chambers, and a drainage tube. The inlet port is positioned at top of the upper chamber, said inlet port in turn is removably connected to a catheter. The breathing open areas between the vertical chambers of said upper and lower chambers allow the urine collection device to conform to shape of patient body. Moreover, the chambers distribute the weight of collected urine equally to avoid a bulging effect. Alternately, the urine collection device has absorbent layer insert to absorb the bodily discharge.

7 Claims, 15 Drawing Sheets

(56) References Cited

U.S. PATENT DOCUMENTS

2017/0056630 A1* 3/2017 Fee ................... A61M 25/02
2017/0079571 A1* 3/2017 Washington ........... A61F 5/441
2017/0100276 A1   4/2017 Joh
2017/0312114 A1* 11/2017 Glithero ........... A61B 5/150366

* cited by examiner

MULTICHAMBERED URINE COLLECTION DEVICE

FIELD OF THE INVENTION

The present invention relates to a novel and smart urine collection device. More particularly, it relates to a smart apparatus for collecting urine in a uniquely designed multi-chambered urine collection device and an additional smart leg device for collecting urine and other body fluids in a more convenient and hygienic way.

BACKGROUND OF THE INVENTION

Urine collection devices are used in health care industry. However, other areas outside the health care industry also find uses for urine collection devices. Hunters, pilots, boaters, any travelers/truck drivers, handicapped individuals would also find urine collection device advantageous. Urine drainage devices collect urine and attached to a catheter (tube) inside the bladder. It is useful for non-urine incontinence patients and ordinary users who have limited toilet options or limited time such as drivers, road travelers, miners, soldiers, security guards, surgeons, pilots, critical site workers, handicapped, special needs and pilgrims, individuals caught in traffic jams or snowstorms to increase their productivity and mobility. Particularly in remote areas, public restrooms are often unavailable. Finding a secluded spot to urinate outdoors is often impossible and sometimes people are concerned regarding sanitation. Growing fears of infection has made people more reluctant to expose themselves to unnecessary health risks.

Urine Bags are used for the collection and temporary storage of urine. It takes the form of Leg Bags, which are strapped to the upper leg, or Drainage Bags, which are usually used while the user is in bed or in a wheelchair. Many Urinal Bags are drainable allowing the urinary patient to continue using the bag for a period of time. When the urine bag is no longer usable or unhygienic, the urinary bag is disposed. Some Urine Drainage Bags may be urine collection bottles that may be reusable.

U.S. Pat. No. 7,931,630 B2 discloses a multi-functional and modular urine collection system which can include a self-expanding container having a receptacle for receiving urine from the tubing, a pump for moving urine through the tubing and into a receptacle, extendable tubing that may be shortened and/or lengthened, and/or one or more meters for monitoring, measuring, transmitting or Storing a characteristic from the urine.

US20170100276 A1 discloses a disposable wearable urinary collection apparatus. The urinary receptacle includes an elongate, tubular main body having a closed upper end and an open lower end; a tubular port in fluid communication with the main body, the tubular port being configured to receive a user's penis therein in a fluid tight manner; a urine collection receptacle connectable to the lower end of the main body which receives and stores the urine therein; and a fastener which secures at least one of the main body and the urine collection receptacle to the user or a garment worn by the user. The apparatus is simple to use and is manually accessible for handling though modified side pockets of a pair of pants or other such conventional garment worn by the user. The main body, tubular port, and storage receptacle are formed of flexible, water-proof material and are configured to collapse flat against a user's body when not in use.

KR20170108266 describes the real time urination amount measurement and test system and its method using the system. The real time urination amount measurement and test system comprises: a measuring unit (101) including a sensor unit (110), a measuring unit (120) generating first data by calculating a result value measured by the sensor unit (110), and a transfer unit (130) transferring the first data to a server unit (140) by using short range wireless communication, wherein the sensor unit (110) comprises a first sensor measuring a urination amount of a patient, collected in a urine collection device (111), and a second sensor semi-quantitatively measuring a chemical component contained in the collected urine; and an analysis unit (102) including the server unit (140). The server unit (140) comprises: a web application (141) generating and displaying the urine data for each patient by processing the first data transferred from the transfer unit (130) and providing an interface for managing the urine data; and a database (142) accumulating and storing the urine data for the each patient. A manager (103) checks and manages the urine data in real time by using the interface of the web application (141) or a mobile application (151) by wire and wireless communications without directly checking the urine collection device (111) for the each patient one by one. Therefore, the manager can conveniently check and manage a urine state of the patient in real time by using the wire and wireless communications without directly checking the urine collection device for the each patient one by one.

Therefore, there is a need to provide a smart urine collection device according to the comfort of patient.

OBJECT OF THE INVENTION

The main object of the present invention is to provide a smart urine collection device for management of urinary incontinence.

Yet another object of the present invention is to provide a multi-chambered flat urine collection device that distributes the urine equally in the chambers to avoid bulging effect.

Yet another object of present invention is to provide a smart leg urine collection device equipped with components not limited to urine measuring tool, watch, sensors to monitor and display the physical and chemical characteristics of urine.

Yet another object of the present invention is to provide urine short with an innovative and flat urine collection device inside a pocket of the short with a connection tube to distribute the weight of collected urine. In an alternate embodiment, this bag is attached by Velcro on the outside layer of the short.

Still another object of the present invention is to provide a smart urine collection device having a measuring unit, transfer unit, storing unit and display unit connected to server unit for managing the state of urine of a patient in real time.

SUMMARY OF THE INVENTION

The present invention relates to a novel and smart urine collection device for management in persons with limited mobility or with limited resources. More particularly, the invention relates to a smart apparatus for collecting urine in a uniquely designed multi-chambered urinary device and an additional smart leg device and for disposing off the urine in a more convenient and hygienic way.

In a preferred embodiment, the present invention provides a user friendly multi-chambered flat urine collection device comprising an inlet port having a non-return valve, an upper chamber further divided into a plurality of vertical chambers, a lower chamber further divided into a plurality of vertical chambers, a plurality of breathing open areas intervening said upper, lower and vertical chambers, and a drainage tube. The inlet port is positioned at top of the upper chamber, said inlet port in turn is removably connected to a catheter. The breathing open areas between the vertical chambers of said upper and lower chambers allow the urine collection device to conform to shape of patient body and hence the patient can run or walk properly carrying the urine collection device. Moreover, the chambers distribute the weight of collected urine equally to avoid a bulging effect. A bulging effect is an effect when a fluid collection device starts to droop in bottom with collection of fluid and exhibits turbulence while the body is in motion.

In yet another embodiment, the present invention provides a smart leg urine collection device incorporated with components including, but not limited to, a flow meter which measures the volume of urine against time, a timer to count the number of times a patient has passed urine, a plurality of sensors including but not limited to a pressure sensor to sense the pressure of urine, a temperature sensor to sense the temperature of collected urine, a pH sensor to sense the pH of collected urine and an alarm to indicate when the volume of collected urine exceeds a threshold value.

In yet another embodiment of the present invention, a urine collection short is provided with an innovative and flat urine collection device engineered inside a pocket of an underwear. The urine collection short comprising two identical urine collection devices on each leg side, a connection tube to distribute urine in urine collection devices.

In yet another embodiment, the present invention provides a smart urine collection system comprising of a measuring unit, a storing unit, a transfer unit, a server unit and a display unit wherein, the measuring unit measures or senses the physical and chemical characteristics of collected urine in the urine collection device using plurality of electronic sensors including but not limited to a temperature sensor, a pressure sensor, a pH sensor etc; the storing unit stores the measured characteristics of collected urine; and a transmission unit to transmit the stored characteristics of urine from storing unit to the server unit through wired and wireless communication for real time monitoring.

In an alternative embodiment, the present invention provides a smart leg urine collection device having an upper chamber, a lower chamber and a double tube connector for Foley catheter. The chambers having plurality of folds which expand three times depending on the volume of urine. The lower chamber of the urine collection device starts filling with urine and the user when sits, the urine accumulated to the lower chamber moves to the upper chamber and once user stands up, urine stays in the upper chamber. This design allows the doubling of flat chambered urine collection device. The flat chamber is enlarged to the top even it is far from the main urine inlet. In an alternate embodiment, the smart leg urine collection device comprises a wearable sock comprising a plurality of holding elements to hold a urine bag in place and a plurality of adjusting elements to adjust to the size of user's shin. The sock can be worn on the shin on sides and the adjusting elements can be used to adjust the sock to fit the user's convenience.

In an alternative embodiment, the present invention provides a urine collection short with an innovative and flat urine collection device engineered inside a pocket of an underwear. The urine collection short comprising two identical urine collection devices on each leg side. The two urine collection devices are connected independently to the catheter hence no interconnection between two urine collection devices is required.

In another preferred embodiment, the present invention provides a double chambered urine collection device to collect urine or body fluids or discharge from a catheter. The urine collection device comprises a urine collecting bag/chamber connected having first end and a second end. The first end is connected to the catheter and the second end is connected to a urine storing bag/chamber. The urine collection bag/chamber comprises at least one chamber having an inlet port at the first end to connect to the catheter, an anti-reflux valve beneath the inlet port, and a drainage tube at the second end to connect to the urine storing bag. The drainage tube includes a drainage valve to control the draining of body fluids. The urine storing bag/chamber comprises a connector at a first end, an absorbent layer insert and a sealing member at a second end. The absorbent layer insert absorbs the body fluid/discharge and is removable from the bag/chamber. The sealing member is a leakproof zipper arrangement allowing user to remove the absorbent insert from the urine storing bag/chamber. The absorbent layer insert continues as an absorbent rope/channel that travels through the connector. The connector at the first end of urine storing bag/chamber is connected to the drainage tube of the urine collection bag/chamber forming a passage for urine collected in the urine collection bag/chamber to urine storage bag/chamber through the absorbent rope. The urine from the urine collection bag/chamber drains to urine storing bag/chamber and gets absorbed into the absorbent layer insert forming disposable gel. Once the absorbent layer insert is full of its capacity, the user can replace it with a new absorbent layer insert. Alternately, the urine storing bag/chamber comprises a connector at a first end, an absorbent layer insert. The urine storing bag/chamber once used can be disposed and replaced when the user is travelling. The urine storing bag/chamber can be of different sizes as per the user's requirement.

DESCRIPTION OF THE INVENTION

Figure 1:
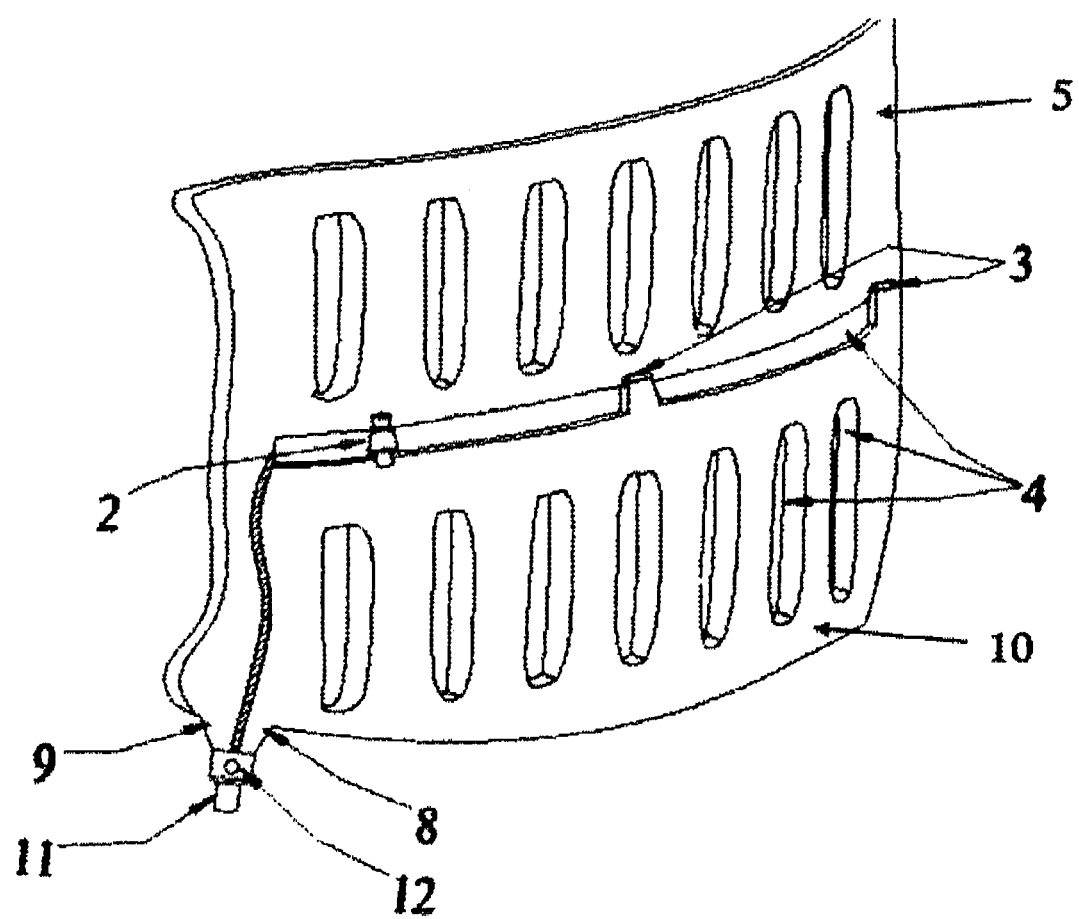
FIG. 1 is a front view of a flat multi-chambered urine device in accordance with an embodiment of the present invention.

Many aspects of the invention can be better understood with references made to the figures below. The components in the figures are not necessarily drawn to scale. Instead, emphasis is placed upon clearly illustrating the components of the present invention. Moreover, like reference numerals designate corresponding parts through the several views in the drawings. Before explaining at least one embodiment of the invention, it is to be understood that the embodiments of the invention are not limited in their application to the details of construction and to the arrangement of the components set forth in the following description or illustrated in the drawings. The embodiments of the invention are capable of being practiced and carried out in various ways. In addition, the phraseology and terminology employed herein are for the purpose of description and should not be regarded as limiting.

In a preferred embodiment, the present invention provides a user friendly multi-chambered flat urine collection device comprising an inlet port having a non-return valve, an upper chamber further divided into a plurality of vertical chambers, a lower chamber further divided into a plurality of vertical chambers, a plurality of breathing open areas intervening said upper, lower and vertical chambers, and a drainage tube. The inlet port is positioned at top of the upper chamber, said inlet port in turn is removably connected to a catheter. The breathing open areas between the vertical chambers of said upper and lower chambers allow the urine collection device to conform to shape of patient body and hence the patient can run or walk properly carrying the urine collection device. Moreover, the chambers distribute the weight of collected urine equally to avoid a bulging effect. A bulging effect is an effect when a fluid collection device starts to droop in bottom with collection of fluid and exhibits turbulence while the body is in motion.

In yet another embodiment, the present invention provides a smart leg urine collection device incorporated with components including, but not limited to, a flow meter which measures the volume of urine against time, a timer to count the number of times a patient has passed urine, a plurality of sensors including but not limited to a pressure sensor to sense the pressure of urine, a temperature sensor to sense the temperature of collected urine, a pH sensor to sense the pH of collected urine and an alarm to indicate when the volume of collected urine exceeds a threshold value.

In yet another embodiment of the present invention, a urine collection short is provided with an innovative and flat urine collection device engineered inside a pocket of an underwear. The urine collection short comprising two identical urine collection devices on each leg side, a connection tube to distribute urine in urine collection devices.

In yet another embodiment, the present invention provides a smart urine collection system comprising of a measuring unit, a storing unit, a transfer unit, a server unit and a display unit wherein, the measuring unit measures or senses the physical and chemical characteristics of collected urine in the urine collection device using plurality of electronic sensors including but not limited to a temperature sensor, a pressure sensor, a pH sensor etc.; the storing unit stores the measured characteristics of collected urine; and a transmission unit to transmit the stored characteristics of urine from storing unit to the server unit through wired and wireless communication for real time monitoring.

In an alternative embodiment, the present invention provides a smart leg urine collection device having an upper chamber, a lower chamber and a double tube connector for Foley catheter. The chambers having plurality of folds which expands three times depending on the volume of urine. The lower chamber of the urine collection device starts filling with urine and the user when sits, the urine accumulated to the lower chamber moves to the upper chamber and once user stands up, urine stays in the upper chamber. This design allows the doubling of flat chambered urine collection device. The flat chamber is enlarged to the top even it is far from the main urine inlet. In an alternate embodiment, the smart leg urine collection device comprises a wearable sock comprising a plurality of holding elements to hold a urine bag in place and a plurality of adjusting elements to adjust to the size of user's shin. The sock can be worn on the shin on sides and the adjusting elements can be used to adjust the sock to fit the user's convenience.

The urine collection device can be a disposable or single use device. Alternately, the device is a reusable device as per the subject to subject requirements.

In another preferred embodiment, the present invention provides a double chambered urine collection device to collect urine or body fluids or discharge from a catheter. The urine collection device comprises a urine collecting bag/chamber connected having first end and a second end. The first end is connected to the catheter and the second end is connected to a urine storing bag/chamber. The urine collection bag/chamber comprises at least one chamber having a first connector at the first end to connect to the catheter, an anti-reflux valve beneath the first connector, and a drainage tube at the second end to connect to the urine storing bag/chamber. The drainage tube includes a drainage valve to control the draining of body fluids. The urine storing bag/chamber comprises a connector at a first end, an absorbent layer insert and a sealing member at a second end. The absorbent layer insert absorbs the body fluid/discharge and is removable from the bag/chamber. The sealing member is a leakproof zipper arrangement allowing user to remove the absorbent insert from the urine storing bag/chamber. The absorbent layer insert continues as an absorbent rope/channel that travels through the connector. The connector at the first end of urine storing bag/chamber is connected to the drainage tube of the urine collection bag/chamber forming a passage for urine collected in the urine collection bag/chamber to urine storage bag/chamber through the absorbent rope. The urine from the urine collection bag drains to urine storing bag/chamber and gets absorbed into the absorbent layer insert forming disposable gel. Once the absorbent layer insert is full of its capacity, the user can replace it with a new absorbent layer insert. Alternately, the urine storing bag/chamber comprises a connector at a first end, an absorbent layer insert. The urine storing bag/chamber once used can be disposed and replaced when the user is travelling. The urine storing bag/chamber can be of different sizes as per the user's requirement.

Now referring to FIG. 1, in an embodiment of the present invention, a user friendly multi-chambered flat urine collection device is provided having a plurality of upper chambers 5, a plurality of lower chambers 10 and breathing open areas 4 intervening said upper and lower chambers. The upper and lower chambers are vertical in nature such that as the vertical chambers of said device starts filling with urine, it starts conforming to shape of patient's body and hence the patient can run or walk properly carrying the urine collection device. A urinary catheter 1 is connected to said urine collection device through the inlet port 2 positioned at the top of the said upper chamber for allowing the urine to collect to the bottom of lower chamber via a one way valve positioned in the breathing open area connecting upper and lower chamber and a one way valve 3 to pass the urine from lower chamber to upper chamber when the patient is sitting or when the lower chamber of urine collection device gets full. When the urine collection device gets full, urine is drained through drainage valve 8, 9 and 12 using drainage tube 11 positioned at the bottom portion of lower chamber for allowing the urine to drain from the upper chambers or lower chambers and both respectively. Moreover, the chambers distribute the weight of urine equally to avoid bulging effect.

Figure 2A:
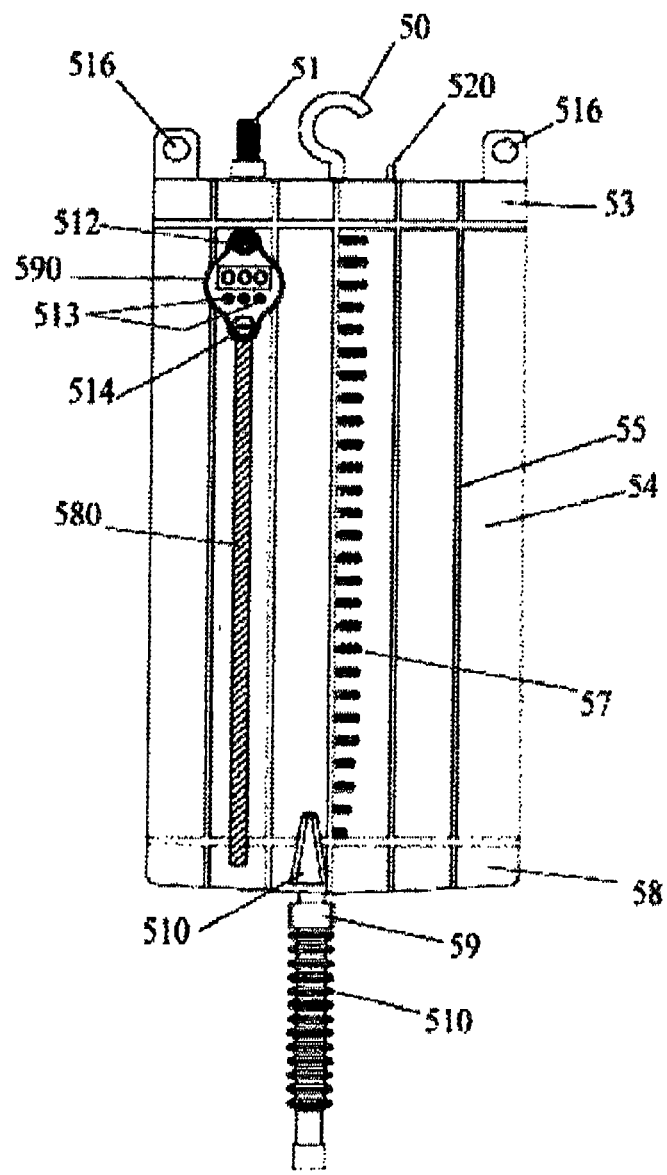
FIGS. 2(a) and 2(b) show a front and back view of the leg smart device in accordance with the embodiment of the present invention.
Figure 2B:
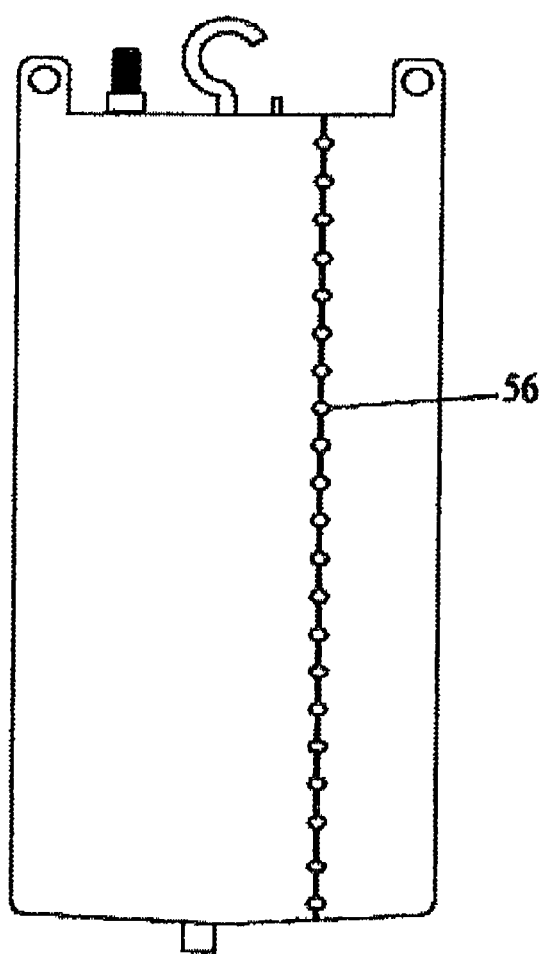

Now referring to FIGS. 2(a) and 2(b), an embodiment of the present invention provides a front and back view of the leg smart urine collection device having a urine tube connection 51 through which urine enters the device from the catheter/urinal. The urine connection tube 51 comprises an anti return vent 52 to avoid leakage of urine or air. The leg smart urine collection device has a similar configuration as a multi-chambered urine collection device having an upper chamber connection 53, a lower chamber connection 59, a plurality of vertical urine chambers having urine chamber back wall 54 and a chamber isolator 55 to isolate various vertical urine chambers. Further the device has an optional multipurpose hook 50 for hanging the device to any desired place using bed hook loop 520 according to the comfort of patient. The said device has also a hanging hook 516. The device also includes but not limited to an inner copper patch 57 and an electronic strap 580 acting as an electronic circuit to sense various characteristics of urine, a volume measurement scale 57 on the outer surface of one of the smart urine device chambers, an emergency air vent 530 to push out the air from the device, a drainage valve 59 to drain the urine using the drainage tube 510 once the device gets full, a small speaker 590 run by a low voltage battery 512 to blow out an alarm when the volume of urine exceeds the threshold value, a digital screen 590 preferably touch screen display to show various characteristics of urine such as temperature, pressure etc. and a screen setting button 514 to set or reset the digital screen 590. The threshold value is the value when the volume of urine reaches 70% of the urine collection device.

Figure 3A:
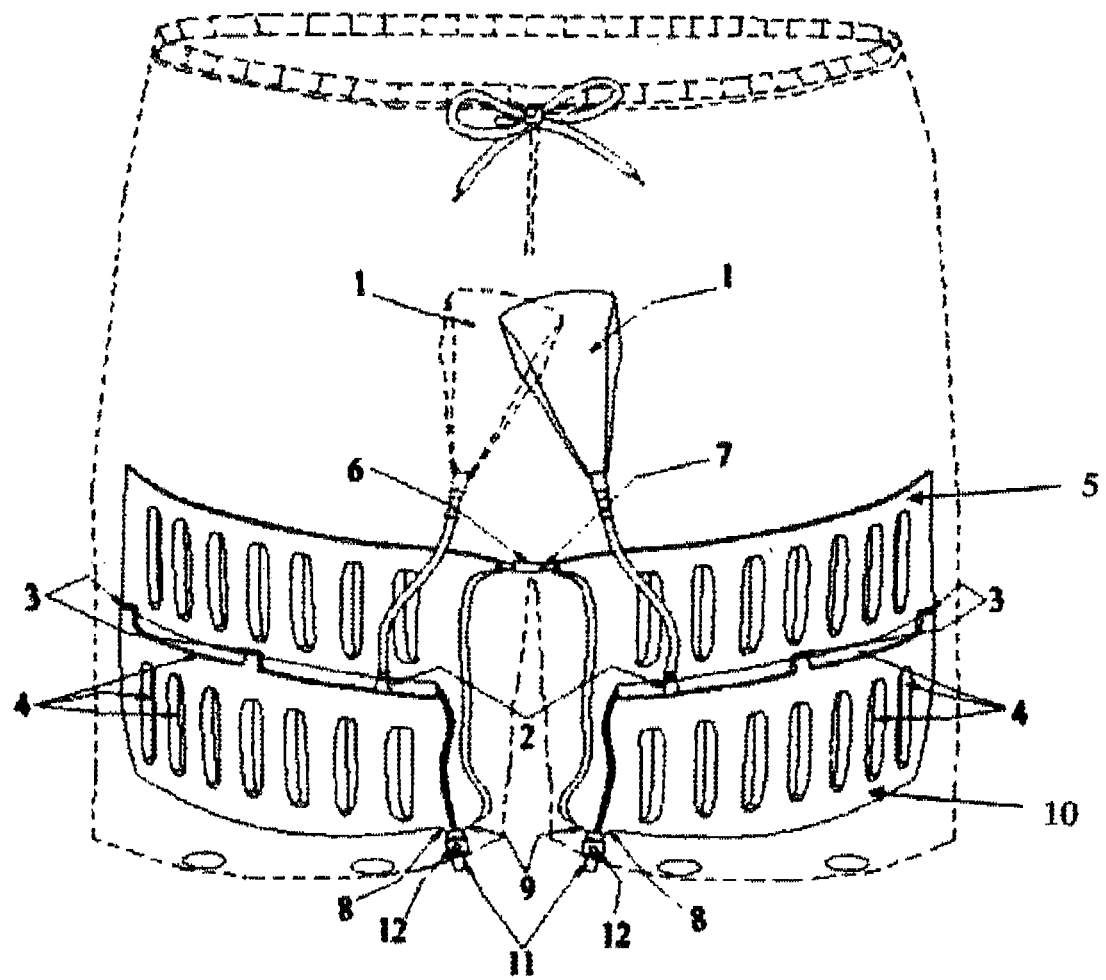
FIGS. 3(a), 3(b), 3(c) 3(d), 3(e), 3(f) and 3(g) show a front view of urine collection shorts with connection tube as connecting pipe, without connection tube, without connection tube but having two inlets, front and back view of the urine collection shorts with the inner T urine tube, front view of the inner T urine tube and top elevation view of the urine collection short in accordance with an embodiment of the present invention.

Now referring to FIG. 3(a) in an embodiment of the present invention provides a front view of urine collection device using connecting pipe as connection tube the urine collection shorts. The connecting pipe 6 between one side and other side of urine collection device and a connector 7 takes care of not spilling the urine from one side of urine collection device to another side of urine collection device. The urinary catheter is connected to said urine collection device through the inlet port 2 positioned at the top of the upper chamber for allowing the urine to collect to the bottom of lower chamber via one way valve positioned in said breathing open area of lower chamber and a one way valve 3 to pass the urine from lower chamber to upper chamber when the patient is sitting. Finally, draining the urine through urine valves 8, 9, 10 using drainage tube 11 of urine collection device and disposing off the urine from the urine outlet provided at the distal end of each leg of the short at interval.

Figure 3B:
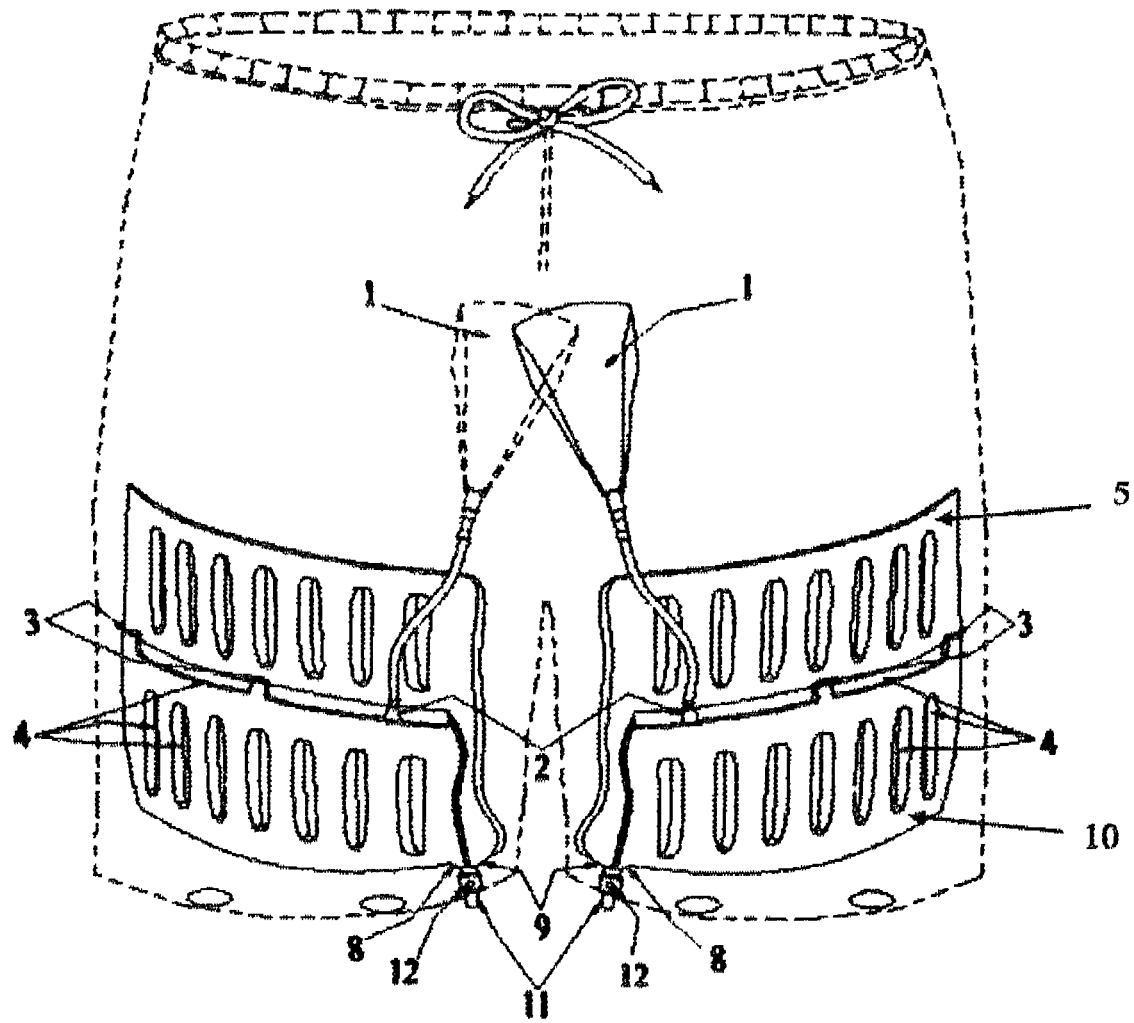

Now referring to FIG. 3(b), in an embodiment of the present invention provides a front view of urine collection device without using connecting pipe. Here the two urine collection devices are acting independently through catheter 1. There is no interconnection between the two urine collection devices. The urinary catheter is connected to said urine collection device through the inlet port 2 positioned at the top of the upper chamber for allowing the urine to collect to the bottom of lower chamber via one way valve 3 positioned in said breathing open area of lower chamber and a one way valve 3 to pass the urine from lower chamber to upper chamber when the patient is sitting. Finally, draining the urine through urine valves 8, 9, 10 using drainage tube 11 of urine collection device and disposing off the urine from the urine outlet provided at the distal end of each leg of the short at interval.

Figure 3C:
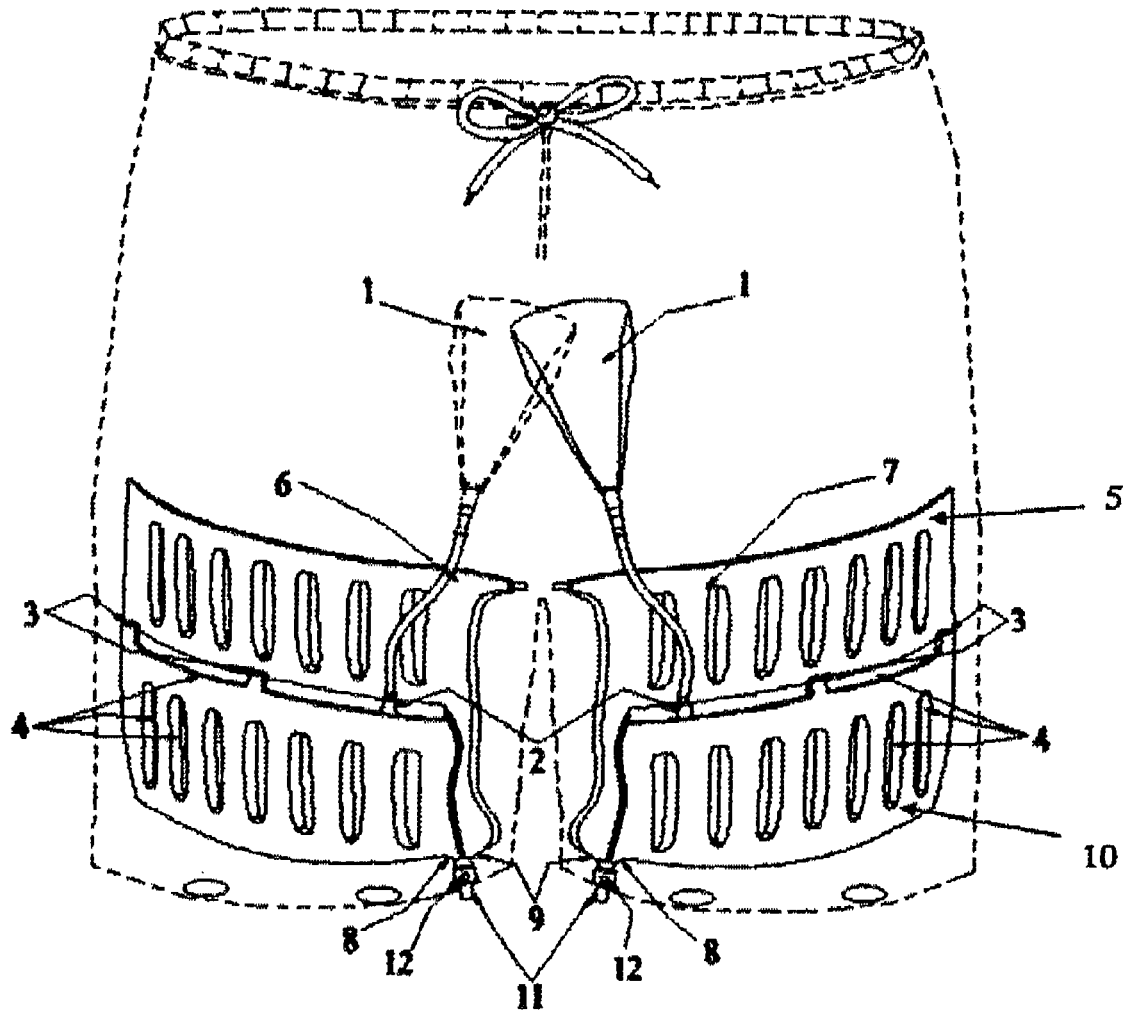

Now referring to FIG. 3(c), in an embodiment of the present invention provides a front view of urine collection device without connection tube and showing two inlets in the upper chamber and lower chamber respectively hence providing ease to the user to attach the catheter to any of the inlets of the urine collection device. More preferably, the Foley catheter and condom catheter is connected to the inlet of upper chamber as these catheters are not very low so can be easily connected to the inlet of upper chamber.

Figure 3D:
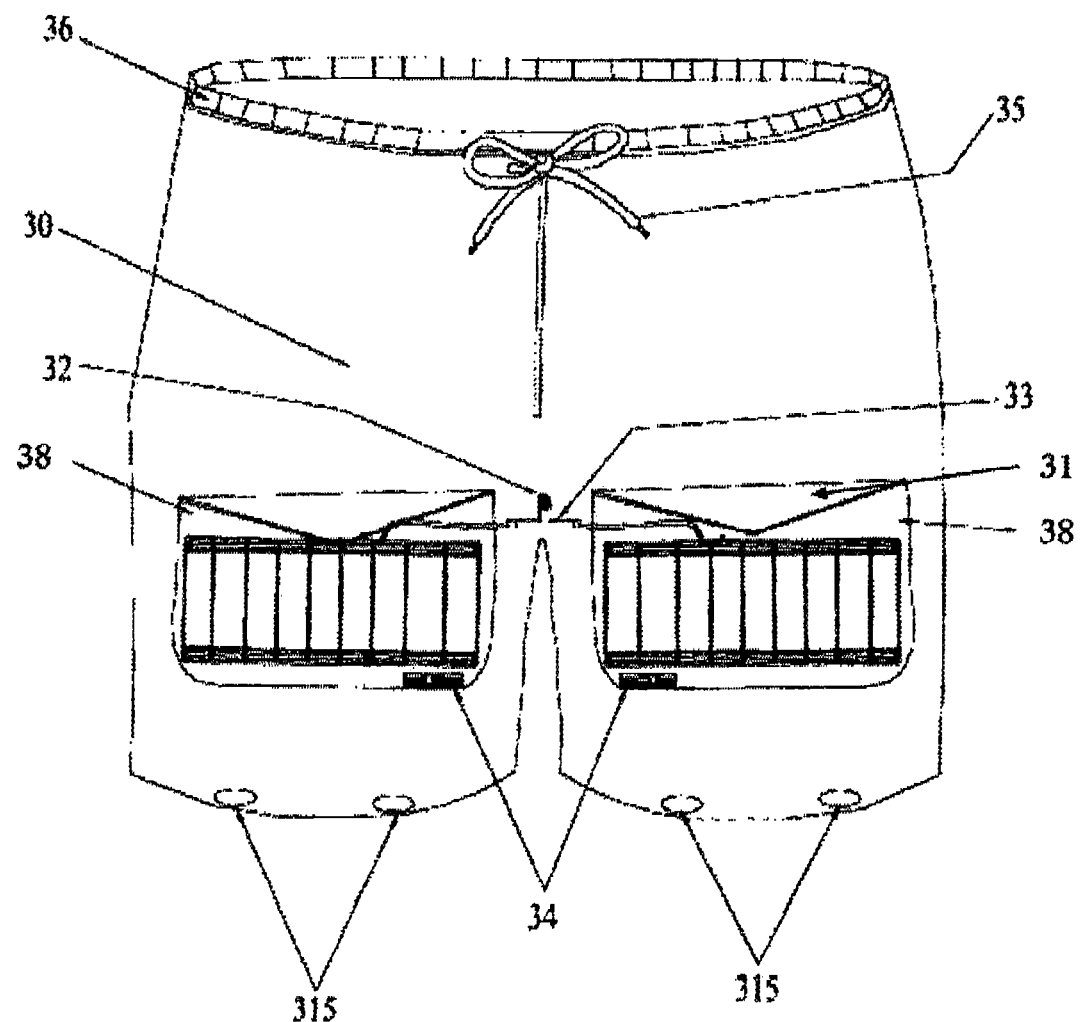
Figure 3E:
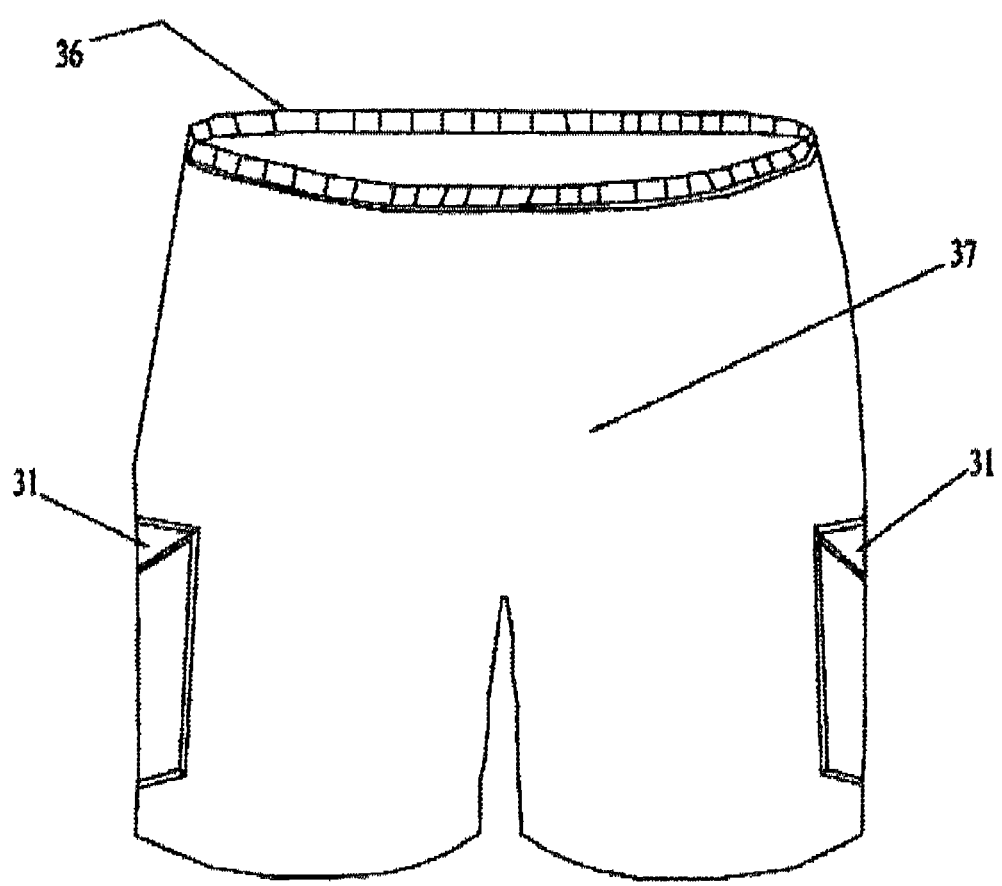

Now referring to FIGS. 3(d) and 3(e) in an embodiment of the present invention provides a front and back view of urine collection shorts 30 respectively with pockets 38 having an opening 31 on both thighs near the groin area to accommodate the specially designed urine collection devices with T urine tube having a separator as connection tube inside the urine collection short 30 to distribute the urine equally in both urine devices preventing a direct pressure on one of the legs and skin. Waist of the short is provided with an elastic band 36 to take the weight of urine as well as fastener so that it can be tied according to the comfort of the wearer. Hooks 315 are provided at the distal end of the short for connection of the extra urine device in the event of severe urinary incontinence and increased volume of urine and disposing off the urine from the urine outlet such as zipper 34 provided at the distal end of each leg of the short at interval.

Figure 3F:
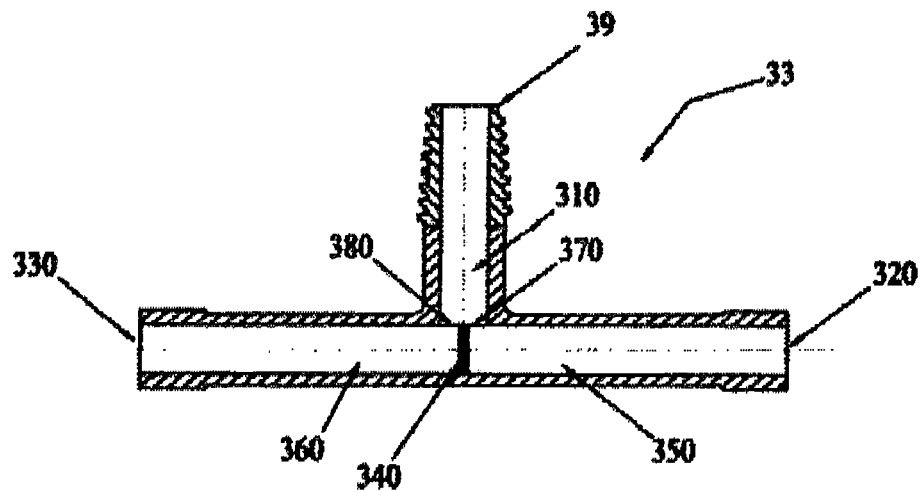

FIG. 3(f) provides front view of the inner T urine tube having connector 39 connected to a catheter/urinal, main urine tube 310 for allowing the urine to enter from the urinal to the T-tube. The T-urine tube has a separator 340 for separating or dividing the urine to left end 370 and right end 380. The urine discharges from the left end 370 to the urine device through the left sub tube end 320 and from the right end 380 to the urine device through the right sub tube end 340.

Figure 3G:
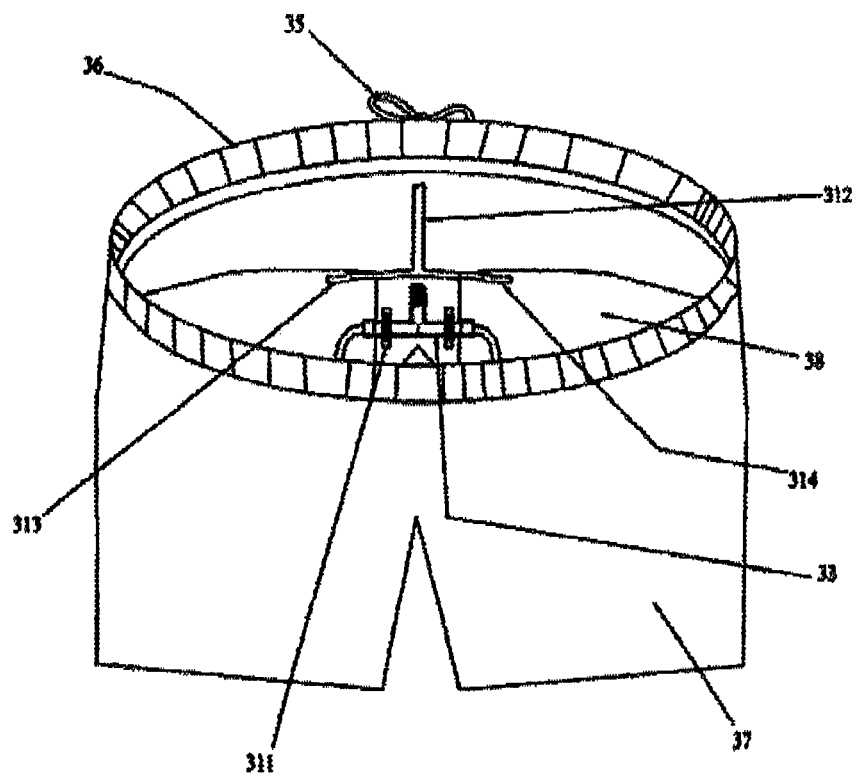

FIG. 3(g) is a top elevation view of the urine collection short showing the back of short 37 having pocket rooms 38 for urine devices. As the urine starts filling the urine device through the T-urine tube via T-urine tube loop 311, the air gets compressed and pushed out from each side through left air tube vent 313 and right air tube vent 314.

Figure 4:
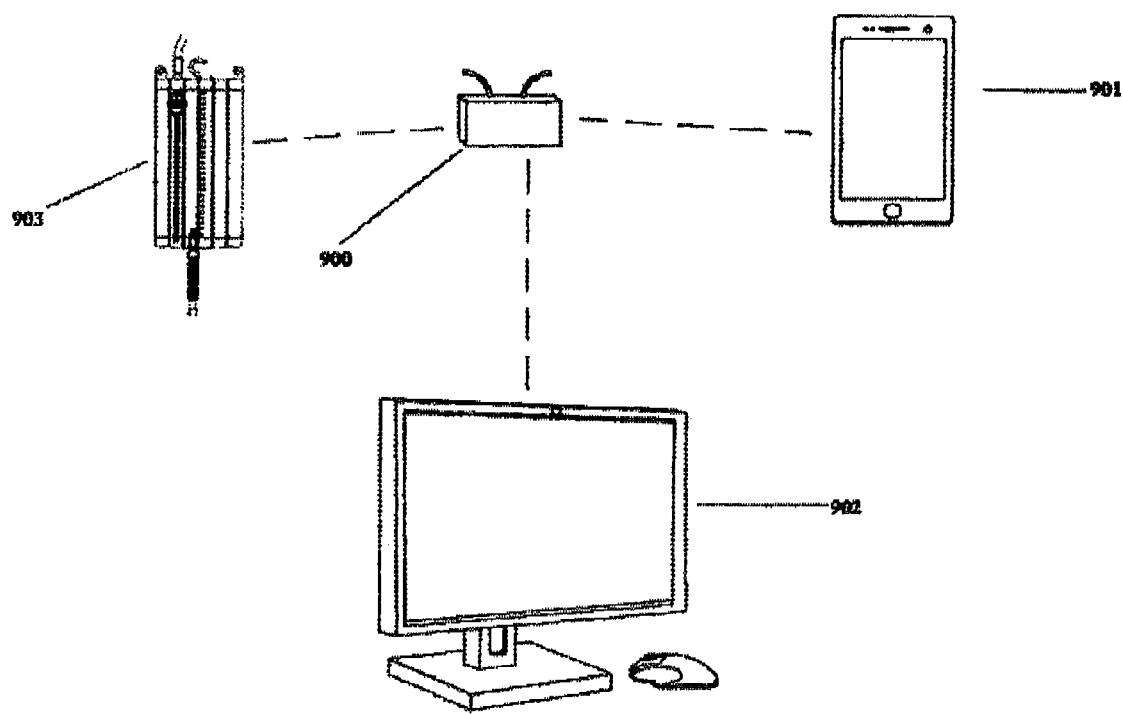
FIG. 4 is a real-time urine quantity measurement and urine examination system in accordance with the embodiment of the present invention.

Now referring to FIG. 4, in an embodiment of the present invention provides a real-time urine quantity measurement and urine examination system. The system comprises of: a urine collection device 903 having a measurement unit with a plurality of sensors including but not limited to temperature sensors, humidity sensor, pH sensor etc. to sense the various characteristics of urine, the transmission unit to transmit the data wire or wirelessly such as Bluetooth transmitter 900 to the server unit, a server unit includes a mobile application 901 or central urine monitoring software to analyze and monitor the characteristic of urine using a Bluetooth receiver, a storing unit such as database for storing the characteristic of urine on server unit and finally a display unit 902 for displaying the required characteristic of characteristic of urine. The characteristic of urine is managed and checked in real time without checking the urine collection device for each patient one by one. The whole system manages the urine state of patient in real time to know the status of each patient by using wire or wireless communication without directly checking the urine collection device of each patient.

Figure 5A:
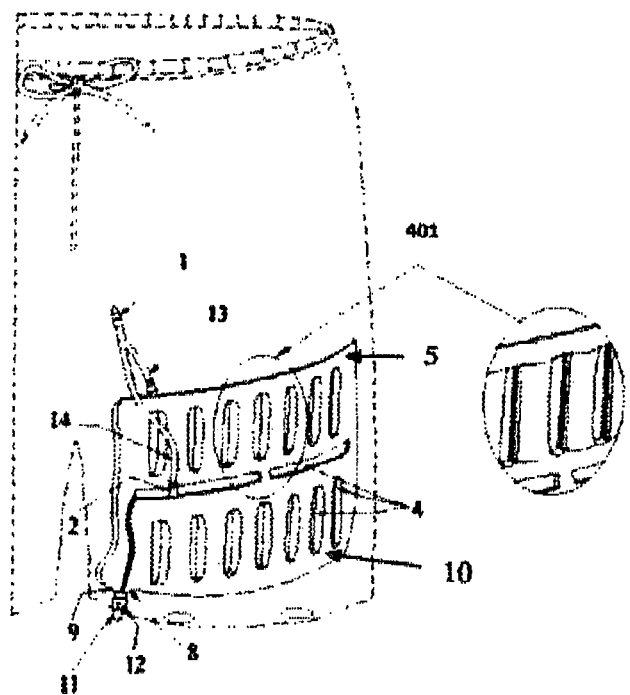
FIGS. 5(a) and 5(b) is a smart leg urine collection device having double connector to Foley or condom catheter and folded chamber in accordance with the embodiment of the present invention.
Figure 5B:
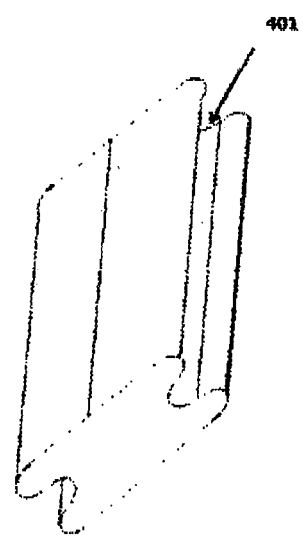

Now referring to FIG. 5(a), in an embodiment of the present invention provides a smart leg urine collection device having an upper chamber, lower chamber, a double tube connector attached to the catheter 1. The chambers having plurality of folds 401 which can expand three times depends on the volume of urine. The double tube connector wherein the one tube of the connector 13 is connected to the upper chamber of urine collection device and the other tube of the connector 14 is connected to the lower chamber of urine collection device. The urine starts filling the urine collection device from the lower chamber. The user when sits, the urine accumulated in the lower chamber moves to the urine chamber and once user stands up, urine stays in the upper chamber. Draining the urine through urine valves 8, 9, 10 using drainage tube 11 of urine collection device and disposing off the urine from the urine outlet provided at the distal end of each leg of the short at interval. FIG. 5(b) shows the plurality of folds 401 in urine collection device. As the urine starts filling the urine collection device, the folded chamber expands depending on the volume of urine.

Figure 6A:
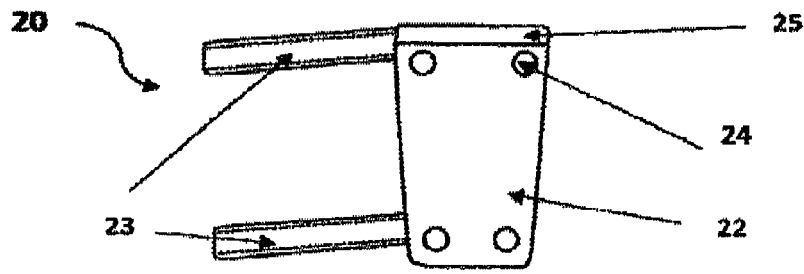
FIGS. 6(a), 6(b), 6(c), 6(d) and 6(e) is an alternate version of smart leg urine collection device in the form of wearable sock as holding device for urine bag.
Figure 6B:
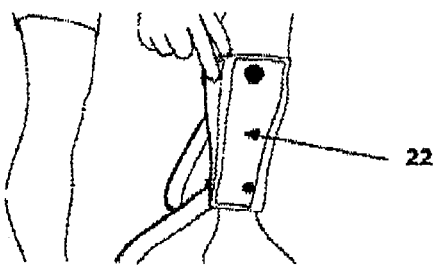
Figure 6C:
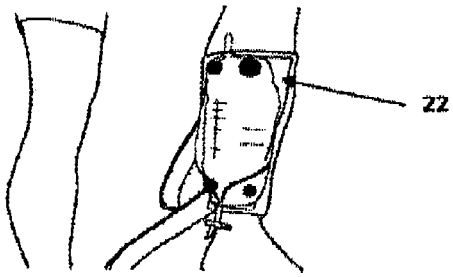
Figure 6D:
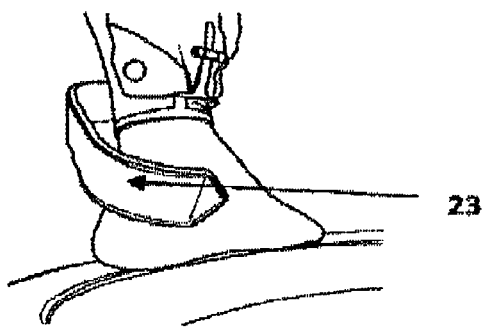
Figure 6E:
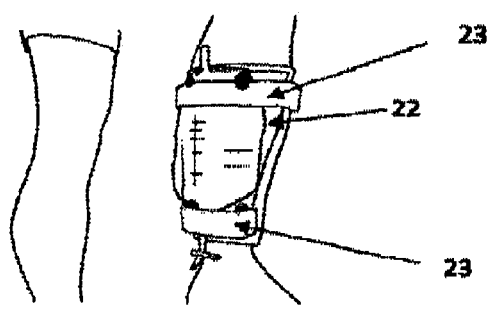

FIG. 6(a) depicts an alternate embodiment of the smart leg urine collection device 20 in the form of wearable sock as holding device for urine bag. The wearable sock 22 comprising an elastic upper portion 25, a plurality of holding elements 24 to hold a urine bag in place and a plurality of adjusting elements 23 to adjust to the size of user's shin. The sock 22 can be worn on the shin on sides as shown in FIG. 6(b). The urine bag is kept in place on sock 22 by plurality of holding elements 24 to avoid dislocation due to urine's weight as shown in FIG. 6(c). FIGS. 6(d) and 6(e) describe the adjusting elements are used to adjust the sock 22 to fit on the shin. The elements include belt & fastening mechanism wherein the belt is used to adjust the fit and can be fastened at desired position around the sock through Velcro or buttons. The holding elements can be buttons/hooks to fasten the removable urine bag from the sock.

Figure 7A:
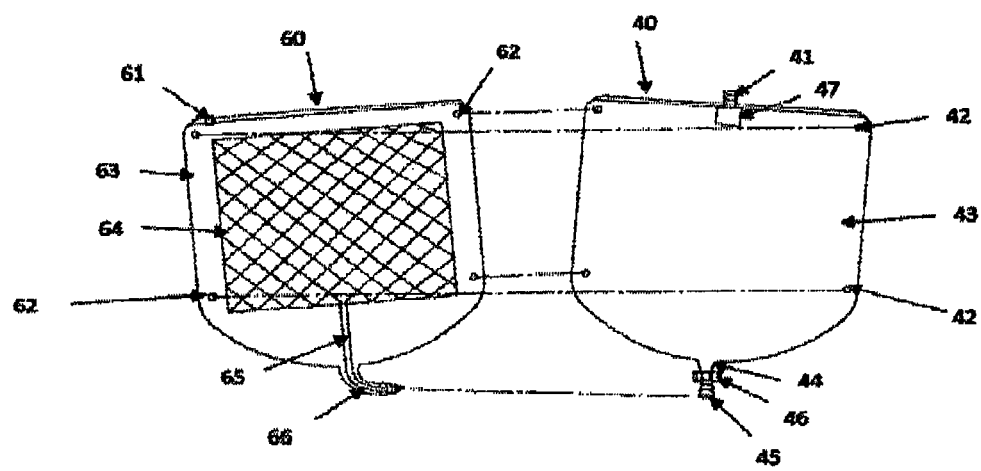
FIGS. 7(a), 7(b), 7(c), 7(d), 7(e) and 7(f) shows a double chambered urine collection device and components.

Referring to FIG. 7(a), a double chambered urine collection device to collect urine or body fluids or discharge is shown. The urine collection device comprises a urine collecting bag/chamber 40 having a first end and a second end. The first end is connected to the catheter (not shown) and the second end is connected to a urine storing bag/chamber 60. The urine collection bag/chamber comprises at least one chamber 43 having an inlet port 41 at the first end to connect to the catheter, an anti-reflux valve 47 beneath the first inlet port 41, and a drainage tube 44 at the second end to connect to the urine storing bag/chamber through a connector 45. The drainage tube includes a drainage valve 46 to control the draining of body fluids. The urine storing bag/chamber comprises a connector 66 at a first end, an absorbent layer insert 64 and a sealing member 61 at a second end. The absorbent layer insert 64 absorbs the body fluid/discharge and is removable from the bag/chamber. The sealing member 61 is a leakproof zipper arrangement allowing user to remove the absorbent insert from the urine storing bag/chamber. The absorbent layer insert continues as an absorbent rope/channel 65 that travels through the connector. The connector at the first end of urine storing bag/chamber is connected to the drainage tube of the urine collection bag forming a passage for urine collected in the urine collection bag/chamber to urine storage bag through the absorbent rope. The urine from the urine collection bag/chamber drains to urine storing bag and gets absorbed into the absorbent layer insert forming disposable gel. Once the absorbent layer insert is full of its capacity, the user can replace it with a new absorbent layer insert. The two bags/chambers are joined via joining means 62 and 42, wherein the chambers are joined side by side such that connector 45 is joined with connector 66. The wall 43 of the urine collecting bag is thin, flat and less flexible to avoid bulging. The wall 63 of urine storing bag are flexible to allow volume of urine in it.

Figure 7B:
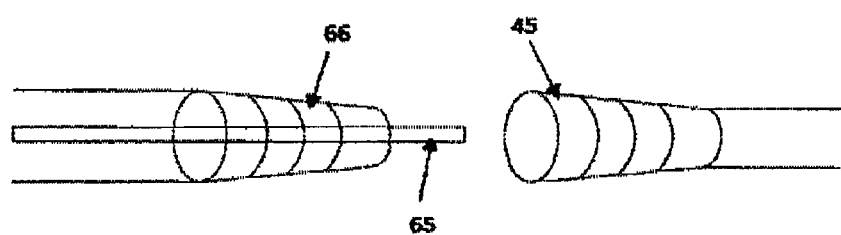
Figure 7C:
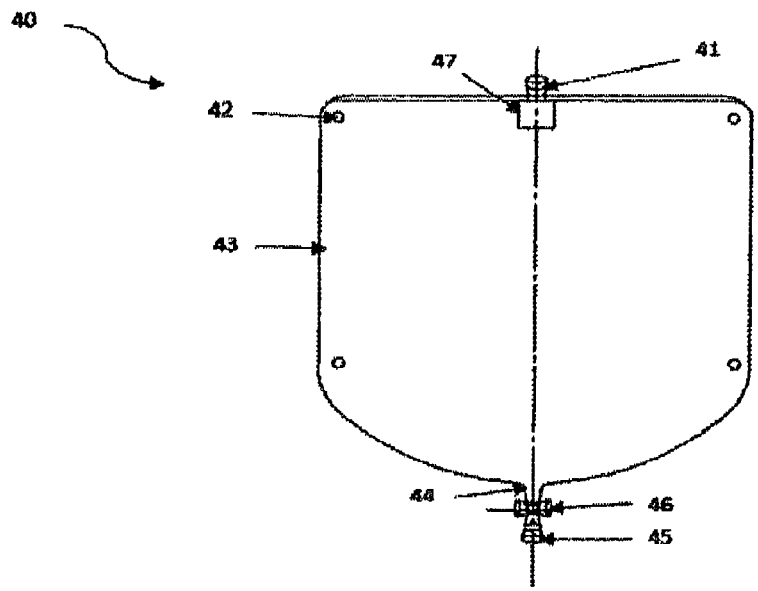
Figure 7D:
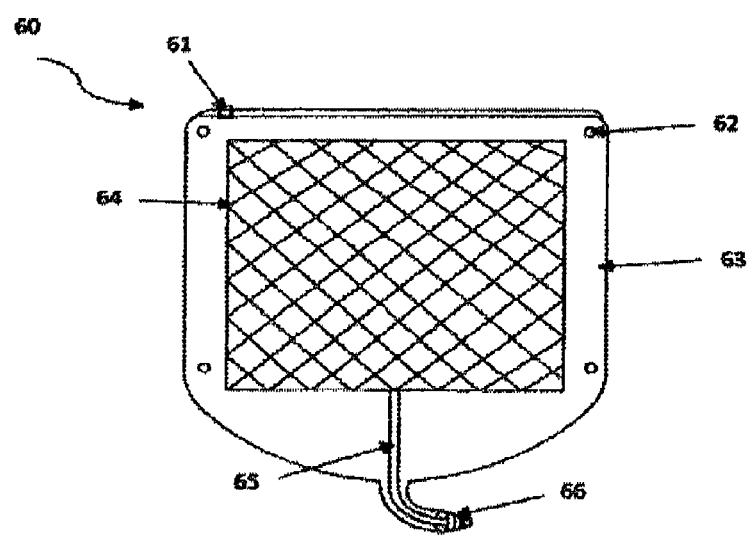
Figure 7E:
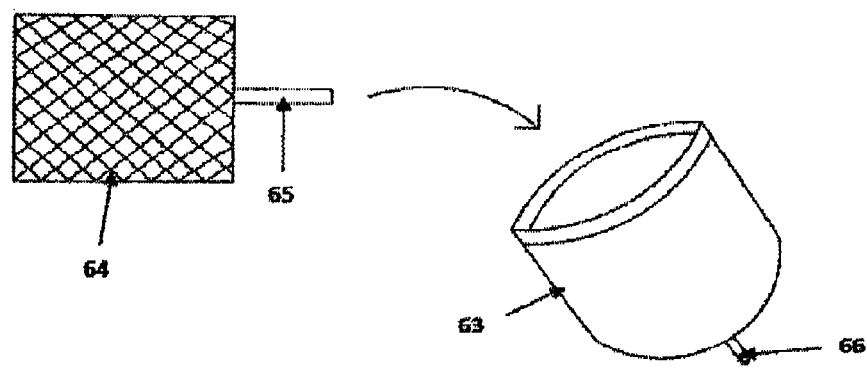
Figure 7F:
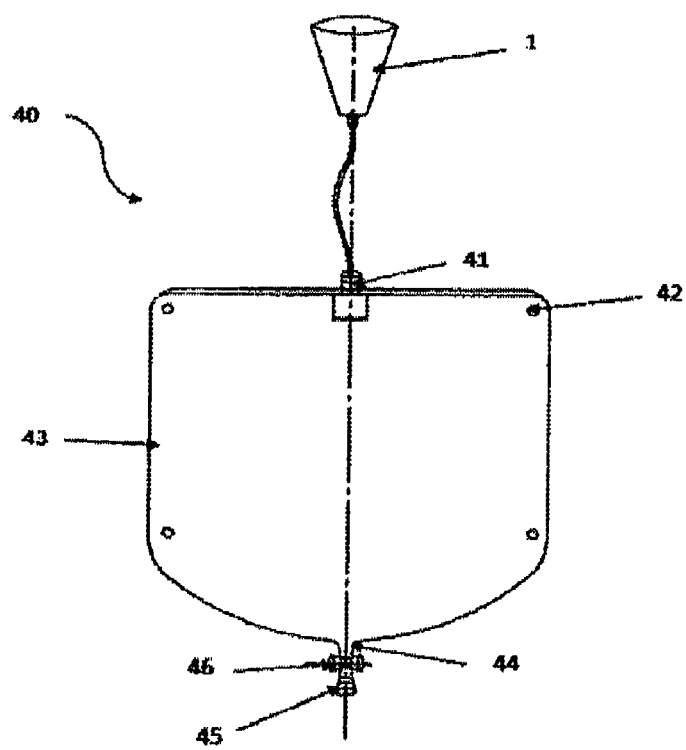

As shown in FIG. 7(b) connector 66 connects to connector 45 with absorbent rope/channel 65 travelling through the connectors. FIG. 7(c) shows urine collecting bag 40. FIG. 7(d) shows urine storing bag with absorbent layer inert 64, while FIG. 7(e) shows the absorbent layer insert 64 with rope 65 removed from the urine storing bag. FIG. 7(f) shows the urine collecting bag connected to a catheter 1.

In a modified version of the double-chambered urine collecting device, the urine storing bag is without a sealing member and is closed at one end. The bag is disposed along with the absorbent layer insert when full of its capacity. This provision is useful for the travelers.

We claim:

1. A multi-chambered mine collection device comprising:
 a) an inlet port (2);
 b) an upper chamber (5);
 c) a lower chamber (10); and
 d) a drainage tube (11);
 wherein,
 the upper chamber (10) is divided into a plurality of vertical chambers having folded side walls;
 the lower chamber (10) is divided into a plurality of vertical chambers having folded side walls;
 a plurality of breathing open areas intervening said upper chamber (5), lower chamber (10) and the vertical chambers of said upper chamber (5) and lower chamber (10);
 the inlet port (2) is positioned at a top of the upper chamber (5), said inlet port (2) in turn is removably connected to a catheter (1);
 the inlet port (1) has a non-return valve;
 the upper chamber (5) is connected to the lower chamber (10) through at least one non-return valve allowing urine to pass from the lower chamber (10) to the upper chamber (5) when a user is sitting or when the lower chamber (10) is full;
 the upper chamber (5) and lower chamber (10) distribute weight of urine equally to avoid bulging; and
 the breathing open areas between the vertical chambers of said upper chamber (5) and lower chamber (10) allow the urine collection device to conform to a user's body shape.

2. The multi-chambered urine collection device as claimed in claim 1, wherein the device further comprises a connecting duct to join a second multichambered urine collection device.

3. A multi-chambered urine collection device comprising:
 a) an inlet port (41);
 b) a urine collecting chamber (43);
 c) a urine storing chamber (60); and
 d) a plurality of joining means (62) to join said urine collecting chamber and said urine storing chamber;
 wherein,
 the urine collecting chamber comprises a drainage tube (44) with a drainage valve (46) and a connector (45);

the urine storing chamber comprises an absorbent layer insert (64) with an absorbent rope (65), a connector (66) and a sealing member (61);

the inlet port is positioned at a top of the urine collecting chamber, said inlet port in turn is removably connected to a catheter (1);

the inlet port (41) has a non-return valve (47);

the urine collecting chamber is connected to the urine storing chamber (60) through the respective connectors of said urine collecting chamber (43) and the urine storing chamber (60) to pass the urine from the urine storing chamber (60) to the urine collecting chamber (43);

the urine collecting chamber (43) has a thin, flat and less flexible wall to distribute weight of urine to avoid bulging;

the urine storing chamber (60) has a flexible wall to allow a volume of urine; and the absorbent layer insert (64) in the urine storing chamber (60) allows the urine collection device to conform to a user's body shape.

4. The multi-chambered urine collection device as claimed in claim 3, wherein the urine storing chamber further comprising a closed end.

5. The multi-chambered urine collection device as claimed in claim 4, wherein the urine storing chamber is a disposable chamber.

6. A wearable urine collection device comprising:
a) a pair of shorts (30) having leg wears, each leg wear having a pocket (38) with at least one orifice at a top and one orifice at a bottom of said pocket (38);
b) at least one multi-chambered urine collection bag in said pocket (38) of said shorts (30), said at least one multi-chambered urine collection bag comprising an inlet port (2), an upper chamber (5), a lower chamber (10), and a drainage tube (11); and
c) an optional distribution means connected to said inlet port (2);

wherein, the upper chamber (5) is divided into a plurality of vertical chambers;

the lower chamber (10) is divided into a plurality of vertical chambers;

a plurality of breathing open areas intervening said upper chamber (5), lower chamber (10) and the vertical chambers of said upper chamber (5) and lower chamber (10);

the inlet port (2) is positioned at a top of the upper chamber (5), said inlet port (2) in turn is removably connected to a catheter;

the inlet port (2) has a non-return valve;

the upper chamber (5) is connected to the lower chamber (10) through at least one non-return valve to allow the urine to pass from the lower chamber (10) to the upper chamber (5) when a patient is sitting or when the lower chamber (10) is full;

the upper chamber (5) and lower chamber (10) distribute weight of urine equally to avoid bulging; the breathing open areas between the vertical chambers of said upper chamber (5) and lower chamber (10) allow the urine collection device to conform to the user's body shape;

the inlet port (2) protrudes out of the orifice at top of the pocket (38);

the drainage tube (11) protrudes out of the orifice at bottom of the pocket (38); and the distribution means is connected to a catheter.

7. The wearable multi-chambered urine collection device as claimed in claim 6, wherein the upper chamber (5) and lower chamber (10) has folded side walls.

\* \* \* \* \*